US00PP28839P3

(12) United States Plant Patent
van Huylenbroeck

(10) Patent No.: US PP28,839 P3
(45) Date of Patent: Jan. 2, 2018

(54) *HIBISCUS* PLANT NAMED 'ILVOPS'

(50) Latin Name: *Hibiscus syriacus*
Varietal Denomination: ILVOPS

(71) Applicant: Johan van Huylenbroeck, Melle (BE)

(72) Inventor: Johan van Huylenbroeck, Melle (BE)

(73) Assignee: Spring Meadow Nursery Inc, Grand Haven, MI (US)

( * ) Notice: Subject to any disclaimer, the term of this patent is extended or adjusted under 35 U.S.C. 154(b) by 31 days.

(21) Appl. No.: 14/998,771

(22) Filed: Feb. 10, 2016

(65) Prior Publication Data

US 2017/0231141 P1 Aug. 10, 2017

(51) Int. Cl.
*A01H 5/02* (2006.01)

(52) U.S. Cl.
USPC ..... Plt./257

(58) Field of Classification Search
USPC ..... Plt./257
CPC ..... A01H 5/02; A01H 5/00
See application file for complete search history.

(56) References Cited

U.S. PATENT DOCUMENTS

PP12,196 P2 * 11/2001 Bellion ..... Plt./257
PP27,285 P2 * 10/2016 Huylenbroeck ..... Plt./257

OTHER PUBLICATIONS

Spring Meadow Nursery, Inc. Flowering Shrubs Stater Plants Catalog and Shrub Reference 2015-2016, retrieved on May 1, 2017, retrieved from Internet at <http://springmeadownursery.com/content-media/catalog_2015.pdf> pp. 1-6, 18, 55.*

* cited by examiner

*Primary Examiner* — June Hwu
(74) *Attorney, Agent, or Firm* — Cassandra Bright

(57) ABSTRACT

A new and distinct *Hibiscus* cultivar named 'ILVOPS' is disclosed, characterized by and heavy blooming of large purple single flowers with a red-purple center eye. Plants do not produce seeds. The new variety is a *Hibiscus*, normally produced as an outdoor garden or container plant.

2 Drawing Sheets

Latin name of the genus and species: *Hibiscus syriacus*. Variety denomination: 'ILVOPS'.

BACKGROUND OF THE INVENTION

The new *Hibiscus* cultivar is a product of a planned breeding program conducted by the inventor, Johan van Huylenbroek, in Melle, Belgium. The objective of the breeding program was to produce new sterile triploid *Hibiscus* varieties. The cross resulting in this new variety was made during 1998.

The seed parent is the unpatented variety *Hibiscus syriacus* 'Purple CV2' (a tetraploid cultivar that was obtained from South Korea). The pollen parent is the patented, commercial variety *Hibiscus syriacus* 'Floru' U.S. Plant Pat. No. 12,196. The new variety was identified as a potentially interesting selection in July of 2001, at a commercial greenhouse in Melle, Belgium.

Asexual reproduction of the new cultivar 'ILVOPS' by vegetative soft wood cuttings was first performed during 2001, at a commercial greenhouse in Melle, Belgium. Subsequent propagation has shown that the unique features of this cultivar are stable and reproduced true to type in 6 successive generations.

SUMMARY OF THE INVENTION

The cultivar 'ILVOPS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ILVOPS' These characteristics in combination distinguish 'ILVOPS' as a new and distinct *Hibiscus* cultivar:

1. Sterile variety, producing no seed.
2. Large, purple single flowers with a red-purple center eye.
3. High flower production per plant.

PARENT COMPARISON

Plants of the new cultivar 'ILVOPS' are similar to plants of the seed parent variety *Hibiscus syriacus* 'Purple CV2' in most horticultural characteristics, however, plants of the new cultivar 'ILVOPS' differ in the following;

1. Smaller flowers than the seed parent.

Plants of the new cultivar 'ILVOPS' are similar to plants of the pollen parent variety *Hibiscus syriacus* 'Floru' U.S. Plant Pat. No. 12,196 in most horticultural characteristics, however, plants of the new cultivar 'ILVOPS' differ in the following;

1. The new variety has a smaller flower than the pollen parent variety.
2. Plants of the new variety are approximately half the height and spread of the pollen parent.
3. Flowers of the new variety are less brightly iridescent than flowers of the pollen parent.

COMMERCIAL COMPARISON

Plants of the new cultivar 'ILVOPS' can be compared to the variety *Hibiscus* 'ILVO347' U.S. Plant Pat. No. 27,285.

These varieties are similar in most horticultural characteristics; however 'ILVOPS' differs in the following:

1. Large purple flowers with red-purple centers. The comparator has large pink flower with red centers.

BRIEF DESCRIPTION OF THE PHOTOGRAPHS

Figure 1:
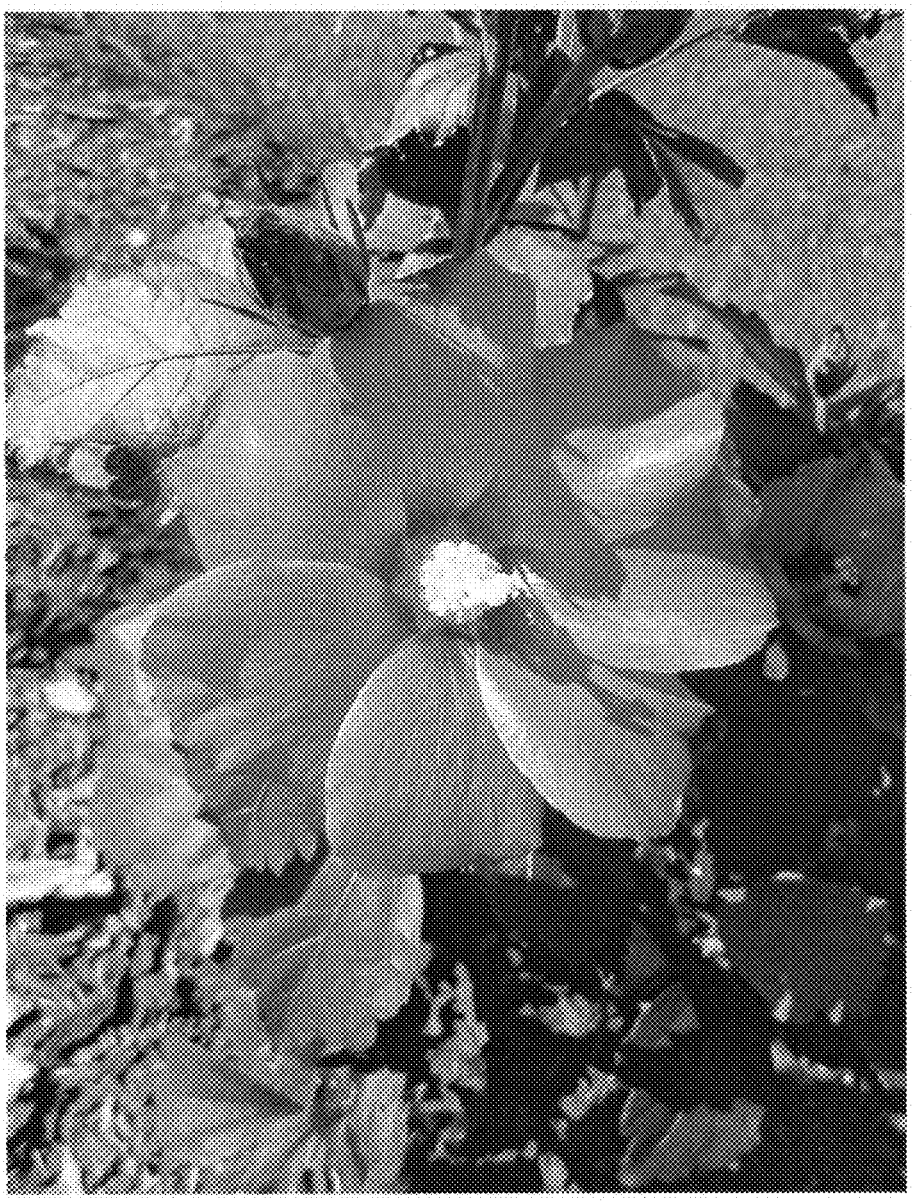

The accompanying photograph in FIG. 1 illustrates in full color a typical flower of 'ILVOPS' grown in an outdoor flower bed, in Grand Haven, Mich.

Figure 2:
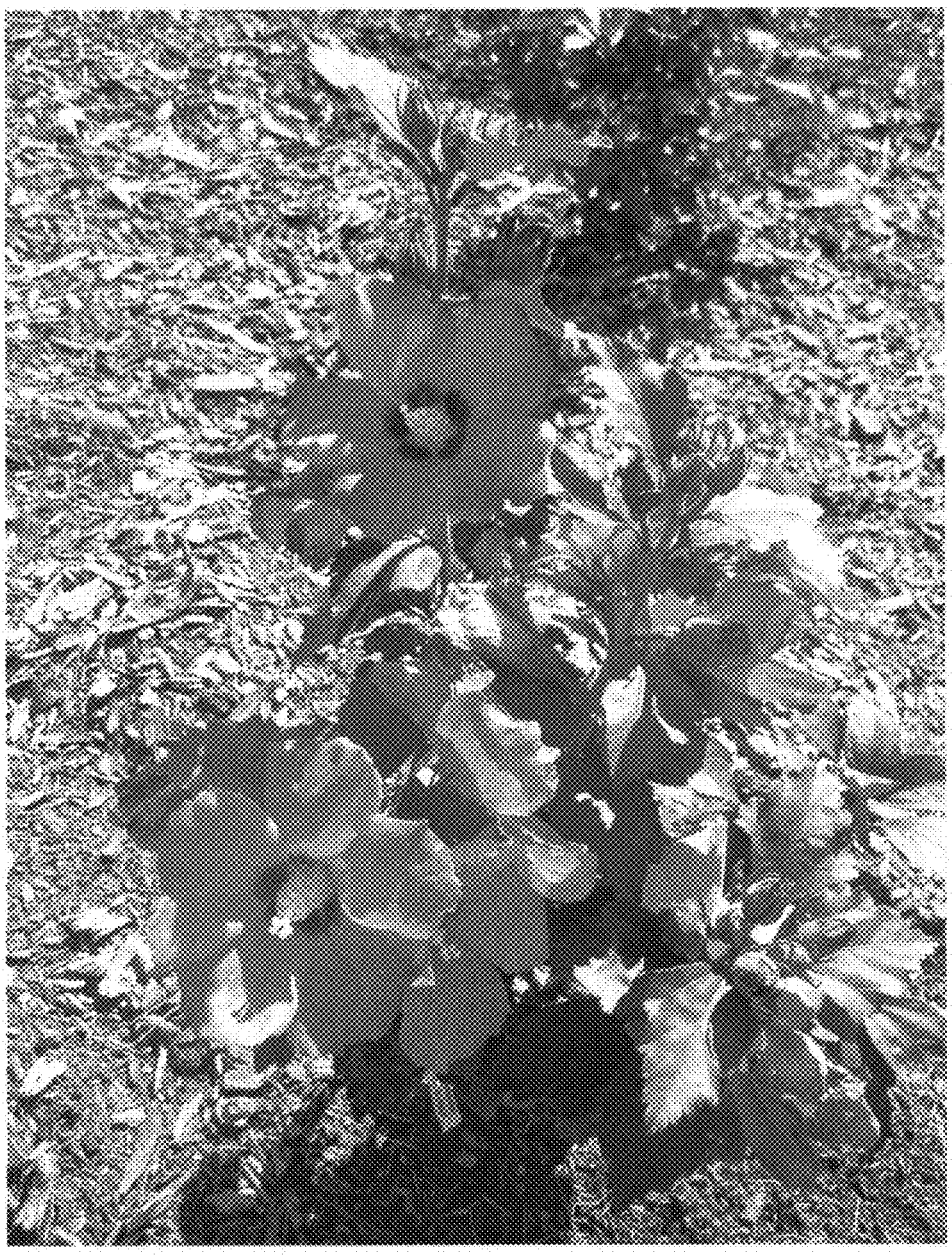

FIG. 2 illustrates in full color a typical plant of 'ILVOPS'. Age of the plant photographed is approximately 1.5 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'ILVOPS' plants grown in a commercial poly greenhouse in Grand Haven, Mich. under natural lighting. Measurements were taken during the July of 2015. The plants were 2 to 3 years old in 3 gallon containers. The growing temperature ranged from 5° C. to 27° C. Measurements and numerical values represent averages of typical plant types.

Botanical classification: *Hibiscus syriacus* 'ILVOPS'.

PROPAGATION

Time to initiate roots: 20 days at approximately 25° C.

Root description: Fibrous, medium root thickness. Tan/brown in color, not effectively measured with a color chart.

Time to produce a rooted young plant: 90 days at 25° C.

PLANT

Plant type: Perennial shrub.
Age of plant described: Approximately 2-3 years old.
Growth habit: Upright.
Pot size of plant described: 3 gallon pot.
Overall plant shape: Upright.
Height: 67 cm.
Plant spread: 72 cm.
Growth rate: Moderate.
Plant vigor: Good.
Branching characteristics: Basal branching. Some pinching required to encourage a denser plant habit.
Length of primary lateral branches: 26.5 cm.
Diameter of lateral branches: 4 mm.
Quantity of lateral branches: 8-10.
Stem:
- *Stem shape*.—Round.
- *Stem strength*.—Moderate.
- *Color*.—Stem: Near RHS Green 141A. Bark: Near RHS Grey-brown 199B.
- *Pubescence*.—Slightly.
- *Angle of attachment*.—25-50° from center of plant.

Internode length: 9 cm on average.

FOLIAGE

Leaf:
- *Arrangement*.—Sub-opposite to alternate, single.
- *Leaf shape*.—Ovate, very shallow lobed.
- *Average length*.—7.3 cm.
- *Average width*.—4.7 cm.
- *Apex*.—Acute.
- *Base*.—Cuneate.
- *Margin*.—Lobed.
- *Texture of top surface*.—Smooth, waxy.
- *Texture of bottom surface*.—Smooth, waxy.
- *Leaf pubescence*.—None.
- *Color*.—Young foliage upper side: Near RHS Green 137A. Young foliage under side: Near RHS Yellow-green 144A. Mature foliage upper side: Near RHS Yellow-green 147A. Mature foliage under side: Near RHS Yellow-green 147B.
- *Venation*.—Pattern: Palmate. Color upper side: Near RHS Yellow-green 147A. Color under side: Near RHS Yellow-green 147A.
- *Petiole*.—Average Length: 2 cm. Diameter: 2 mm. Petiole color upper side: Near RHS Green 137B. Petiole color lower side: Near RHS Green 137B. Petiole Texture upper side: Smooth; pubescent. Petiole Texture lower side: Smooth.

FLOWER

Natural flowering season: Early June through Summer.
Flowering form: Single rotate.
Flower habit: Terminal.
Flower longevity on plant: About 2-3 days.
Flower longevity as a cut flower: About 1 day.
Quantity of flowers per plant: About 100.
Flowers per lateral branch: 8 to 12.
Flower shape: Rotate.
Rate of flower opening: Fast/Moderate.
Flower habit: Single.
Flower aspect: Outward/upright.
Size:
- *Length*.—5 cm.
- *Diameter*.—5 cm.
- *Depth*.—5 cm.

Flower other characteristics:
- *Persistence*.—Self-cleaning.
- *Fragrance*.—None.

Bud:
- *Shape*.—Rounded cone.
- *Length*.—Immature: 2 cm. Mature 3.5 cm.
- *Diameter*.—Immature: 1.5 mm. Mature 2.5 cm.
- *Color*.—Immature: Near RHS Violet-blue 91D. Mature: Near RHS Purple 78A.

Petal:
- *Petal arrangement*.—Whorled, slightly overlapping.
- *Number of petals per flower*.—6 to 7.
- *Fused*.—No.
- *Petal shape*.—Obovate.
- *Petal base*.—Truncate.
- *Margin*.—Entire.
- *Tip shape*.—Rounded with irregular shallow incisions.
- *Length*.—6 cm.

*Width.*—5.5 cm.
*Texture.*—Upper: Smooth/leather; waxy. Lower: Waxy; with prominent smooth veins.

Petal color:
*When opening.*—Upper surface: Near RHS Purple-violet 80B; Red-purple 59A near base of petal, forming a small dark flower eye. Short flower eye extension. Lower surface: Near RHS Purple 78B.
*Fully opened.*—Upper surface: Near RHS Purple 78B; Red-purple 59A near base of petal, forming a small dark flower eye. Short flower eye extension. Lower surface: Near RHS Purple 78B.
*Fading to.*—Upper surface: Near RHS Purple 78A with veins and margin fading to Purple 79A, forming a small dark flower eye. Short flower eye extension. Lower surface: Near RHS Purple 78A with veins and margin fading to Purple 79A.

Sepal:
*Arrangement.*—Radial; forming a star shaped calyx.
*Number.*—6.
*Shape.*—Ovate.
*Tip.*—Aristate.
*Base.*—Fused.
*Margin.*—Entire.
*Length.*—3 cm.
*Width.*—1 cm.
*Texture, upper.*—Rough; slightly pubescent.
*Texture, lower.*—Smooth; waxy
*Color.*—Upper surface at maturity: Calyx: Near RHS Yellow-green 144A; Epicalyx: Near RHS Green 137A. Under surface at maturity: Calyx: Near RHS Yellow-green 145A; Epicalyx: Near RHS Green 137A.

Calyx:
*Shape.*—Calyx: Ovate; star. Epicalyx: Acicular, single.
*Length.*—Calyx: 3 cm. Epicalyx: 3 cm.
*Diameter.*—Calyx: 1 cm. Epicalyx: 2 cm.

Peduncle:
*Length.*—4 cm.
*Diameter.*—5 mm.
*Color.*—Near RHS Yellow-Green 146B.
*Orientation.*—25°.
*Strength.*—Moderate.
*Texture.*—Rough/waxy; pubescent.

REPRODUCTIVE ORGANS

Stamens:
*Number.*—About 45.
*Filament length.*—3 mm.
*Filament color.*—Near RHS White 155B.

Anthers:
*Shape.*—Oval lobed.
*Length.*—4 mm.
*Color.*—Near RHS Greyed-yellow 160C.
*Pollen color.*—Near RHS White 155B.
*Pollen amount.*—Some.

Pistil:
*Number.*—1.
*Length.*—0.5-1 cm.
*Style.*—Length: 3 cm. Color: Near RHS White 155B.
*Stigma.*—Shape: Overall round, composed of 5 to 6 lobes. Color: Near RHS White 155A.
*Ovary color.*—Near RHS White 155B.

OTHER CHARACTERISTICS

Seeds and fruits: Not observed.

Disease/pest resistance: Neither resistance nor susceptibility to normal diseases and pests of *Hibiscus* have been observed.

Garden performance: Good tolerance, performs well in harsh weather.

Temperature tolerance: The new variety tolerates temperatures between −26° C. to 35° C.

What is claimed is:

1. A new and distinct cultivar of *Hibiscus* plant named 'ILVOPS' as herein illustrated and described.

* * * * *